(12) United States Patent
Smolko et al.

(10) Patent No.: US 7,314,542 B2
(45) Date of Patent: Jan. 1, 2008

(54) METHODS AND MATERIALS FOR OPTIMIZATION OF ELECTRONIC TRANSPORTATION AND HYBRIDIZATION REACTIONS

(75) Inventors: Daniel D. Smolko, Jamul, CA (US); Paul D. Swanson, Santee, CA (US); Dalibor Hodko, Poway, CA (US); David Canter, San Diego, CA (US); Robert W. Haigis, San Diego, CA (US); Tricia Patterson, San Diego, CA (US)

(73) Assignee: Nanogen, Inc., San Diego, CA (US)

( * ) Notice: Subject to any disclaimer, the term of this patent is extended or adjusted under 35 U.S.C. 154(b) by 33 days.

(21) Appl. No.: 11/234,054

(22) Filed: Sep. 22, 2005

(65) Prior Publication Data
US 2006/0065531 A1    Mar. 30, 2006

Related U.S. Application Data

(60) Provisional application No. 60/613,148, filed on Sep. 23, 2004.

(51) Int. Cl.
*G01N 27/447* (2006.01)
(52) U.S. Cl. .......................... 204/450; 204/409; 435/6
(58) Field of Classification Search ........ 204/450–470, 204/600–621; 435/6
See application file for complete search history.

(56) References Cited

U.S. PATENT DOCUMENTS 2,721,171 A    10/1955    Arnold et al.
3,950,738 A    4/1976    Hayashi et al.
3,995,190 A    11/1976    Salgo et al.
4,225,410 A    9/1980    Pace
4,283,773 A    8/1981    Daughton et al.
4,465,770 A *  8/1984    Modrovich ............... 435/12
4,537,861 A    8/1985    Elings et al.
4,563,419 A    1/1986    Ranki et al.
4,580,895 A    4/1986    Patel et al.
4,584,075 A    4/1986    Goldstein et al.
4,594,135 A    6/1986    Goldstein
4,661,451 A    4/1987    Hansen (Continued)

FOREIGN PATENT DOCUMENTS

EP    0228075 A2    7/1987

(Continued)

OTHER PUBLICATIONS

JPO English language computer translation of Yoshihro (JP 09-145673 A), 1997.*

(Continued)

*Primary Examiner*—Alex Noguerola
(74) *Attorney, Agent, or Firm*—O'Melveny & Myers LLP

(57) ABSTRACT

Methods for the transport and hybridization of a nucleic acid on an electrode device by providing a low conductivity buffer with a reducing agent to the device. The low conductivity buffer may also contain a zwitterion. A current and voltage is applied to a location of the device to effect electrophoretic transportation of the nucleic acid towards the location. The nucleic acid is then hybridized to a nucleic probed located at the location. The reducing agent in the low conductivity buffer may also be acting as a chaotropic agent.

19 Claims, 8 Drawing Sheets

Histidine Stabilization

U.S. PATENT DOCUMENTS

| | | | |
|---|---|---|---|
| 4,731,325 A | 3/1988 | Palva et al. |
| 4,751,177 A | 6/1988 | Stabinsky |
| 4,787,963 A | 11/1988 | MacConnell |
| 4,807,161 A | 2/1989 | Comfort et al. |
| 4,816,418 A | 3/1989 | Mack et al. |
| 4,822,566 A | 4/1989 | Newman |
| 4,828,729 A | 5/1989 | Klevan et al. |
| 4,908,112 A | 3/1990 | Pace |
| 4,936,963 A | 6/1990 | Mandecki et al. |
| 5,063,081 A | 11/1991 | Cozzette et al. |
| 5,064,519 A | 11/1991 | Tice, Jr. et al. |
| 5,074,977 A | 12/1991 | Cheung et al. |
| 5,075,077 A | 12/1991 | Durley, III et al. |
| 5,096,669 A | 3/1992 | Lauks et al. |
| 5,096,807 A | 3/1992 | Leaback |
| 5,110,434 A | 5/1992 | Zhu et al. |
| 5,114,674 A | 5/1992 | Stanbro et al. |
| 5,125,748 A | 6/1992 | Bjornson et al. |
| 5,126,022 A | 6/1992 | Soane et al. |
| 5,143,854 A | 9/1992 | Pirrung et al. |
| 5,151,189 A | 9/1992 | Hu et al. |
| 5,164,319 A | 11/1992 | Hafeman et al. |
| 5,166,063 A | 11/1992 | Johnson |
| 5,192,405 A | 3/1993 | Petersen et al. |
| 5,200,051 A | 4/1993 | Cozzette et al. |
| 5,202,231 A | 4/1993 | Drmanac et al. |
| 5,219,726 A | 6/1993 | Evans et al. |
| 5,227,265 A | 7/1993 | DeBoer et al. |
| 5,234,566 A | 8/1993 | Osman et al. |
| 5,242,797 A | 9/1993 | Hirschfeld |
| 5,304,487 A | 4/1994 | Wilding et al. |
| 5,312,527 A | 5/1994 | Mikkelsen et al. |
| 5,412,087 A | 5/1995 | McGall et al. |
| 5,433,819 A | 7/1995 | McMeen |
| 5,434,049 A | 7/1995 | Okano et al. |
| 5,436,129 A | 7/1995 | Stapleton et al. |
| 5,436,170 A | 7/1995 | Cornell et al. |
| 5,445,525 A | 8/1995 | Broadbent et al. |
| 5,445,934 A | 8/1995 | Fodor et al. |
| 5,464,517 A | 11/1995 | Hjerten et al. |
| 5,468,646 A | 11/1995 | Mattingly et al. |
| 5,516,698 A | 5/1996 | Begg et al. |
| 5,527,670 A | 6/1996 | Stanley |
| 5,593,838 A | 1/1997 | Zanzucchi et al. |
| 5,605,662 A | 2/1997 | Heller et al. |
| 5,632,957 A | 5/1997 | Heller et al. |
| 5,653,939 A | 8/1997 | Hollis et al. |
| 5,660,701 A | 8/1997 | Gruska et al. |
| 5,667,667 A | 9/1997 | Southern |
| 5,681,751 A | 10/1997 | Begg et al. |
| 5,726,026 A | 3/1998 | Wilding et al. |
| 5,744,305 A | 4/1998 | Fodor et al. |
| 5,750,015 A | 5/1998 | Soane et al. |
| 5,789,167 A | 8/1998 | Konrad |
| 5,827,482 A | 10/1998 | Shieh et al. |
| 5,849,486 A | 12/1998 | Heller et al. |
| 5,853,668 A | 12/1998 | Begg et al. |
| 5,929,206 A | 7/1999 | Heller et al. |
| 5,965,452 A | 10/1999 | Kovacs |
| 6,013,166 A | 1/2000 | Heller et al. |
| 6,017,696 A | 1/2000 | Heller et al. |
| 6,048,690 A | 4/2000 | Heller et al. |
| 6,051,380 A | 4/2000 | Sosnowski et al. |
| 6,054,270 A | 4/2000 | Southern |
| 6,129,828 A | 10/2000 | Sheldon et al. |
| 6,238,624 B1 | 5/2001 | Heller et al. |
| 6,245,508 B1 | 6/2001 | Heller et al. |
| 6,444,111 B1 | 9/2002 | Montgomery |
| 6,518,022 B1 | 2/2003 | Sosnowski et al. |
| 6,582,660 B1 | 6/2003 | Heller et al. |
| 6,780,584 B1 | 8/2004 | Edman et al. |

FOREIGN PATENT DOCUMENTS

| | | | |
|---|---|---|---|
| GB | 2247889 A | | 3/1992 |
| JP | 09-145673 A | * | 6/1997 |
| WO | WO 86/03782 A1 | | 7/1986 |
| WO | WO 90/01564 A1 | | 2/1990 |

OTHER PUBLICATIONS

Abrams, et al., "Comprehensive Detection Of Single Base Changes In Human Genomic DNA Using Denaturing Gradient Gel Electrophoresis and a GC Clamp", Genomics, vol. 7, No. 4, Aug. 1990, 463-475.

Anand, et al., "Pulsed Field Gel Electrophoresis", *Gel Electrophoresis Of Nucleic Acids—A Practical Approach*, 2d Ed., D. Rickwood and B.D. Hames (New York: IRL Press), 1985, 101-123.

Anderson, et al., "Quantitative Filter Hybridization", *Nucleic Acid Hybridization—A Practical Approach*, Eds. B.D. Hames and S.J. Higgins (Washington D.C.: IRL Press), 1985, 73-111.

Bains, "Setting a Sequence To Sequence A Sequence", Bio/Technology, vol. 10, Jul. 1992, 757-758.

Baringa, "Will 'DNA Chip' Speed Genome Initiative?", Science, vol. 253, Sep. 27, 1991, 1489.

Beattie, et al., "Genosensor Technology", The 1992 San Diego Conference: Genetic Recognition, Nov. 1992, 1-5.

Beltz, et al., "Isolation Of Multigene Families and Determination Of Homologies By Filter Hybridization Methods", Methods In Enzymology, vol. 100, 1983, 266-285.

Brown, et al., "Electrochemically Induced Adsorption Of Radio-Labeled DNA On Gold and HOPG Substrates For STM Investigations", Ultramicroscopy, vol. 38, 1991, 253-264.

Conner, et al., "Detection of Sickle Cell $\beta^S$ -globin Allele By Hybridization With Synthetic Olgionucleotides", Proc. Natl. Acad. Sci. USA, vol. 80, Jan. 1983, 278-282.

Drmanac, et al., "Sequencing of Megabase Plus DNA By Hybridization: Theory of the Method", Genomics, vol. 4, 1989, 114-128.

Drmanac, et al., "DNA Sequence Determination By Hybridization: A Strategy For Efficient Large-Scale Sequencing", Science, vol. 260, Jun. 11, 1993, 1649-1652.

Edman, et al., "Electric Field Directed Nucleic Acid Hybridization On Microchips", Nucleic Acids Research, vol. 25, No. 24, 1997, 4907-4914.

Eggers, et al., "Biochip Technology Development", BioChip Technology Development, Lincoln Laboratory Technical Report 901, Nov. 9, 1990, 1-56.

Fiaccabrino, et al., "Array Of Individually Addressable Microelectrodes", Sensors and Actuators B, vol. B19, 1994, 675-677.

Fodor, et al., "Light-Directed, Spatially Addressable Parallel Chemical Synthesis", Science, vol. 251, 1992, 767-773.

Fodor, et al., Multiplexed Biochemical Assays With Biological Chips, Nature, vol. 364, Aug. 5, 1993, 555-556.

Horejsi, et al., "Some Theoretical Aspects Of Affinity Electrophoresis", Journal of Chromatography, vol. 178, 1979, 1-13.

Horejsi, et al., "Determination Of Dissociation Constants Of Lectin Sugar Complexes By Means Of Affinity Electrophoresis", Biochimica et Biophysica Acta, vol. 499, 1977, 290-290-300.

Kakerow, et al., "A Monolithic Sensor Array Of Individually Addressable Microelectrodes", Sensors and Actuators A, 1994, 296-301.

Mandecki, et al., "High-Resolution Polyacrytamide Gel Electrophoresis Of Oligonucleotides Using L-Histidine Buffer", DNA, vol. 7, No. 1, 1988, 57-62.

Matthews, et al., "Analytical Strategies For The Use of DNA Probes", Analytical Biochemistry, vol. 169, 1988, 1-25.

Palecek, "New Trends In Electrochemical Analysis of Nucleic Acids", Biochemistry and Bioenergetics, vol. 20, 1988, 179-194.

Ranki, et al., "Sandwich Hybridization As A Convenient Method For the Dection of Nucleic Acids In Crude Samples", Gene, vol. 21, 1983, 77-85.

Saiki, "Amplification Of Genomic DNA" *PCR Protocols: A Guide To Methods and Applications*, (Academic Press, Inc.), 1990, 13-20.

Sosnowski, et al., "Rapid Determination Of Single Base Mismatch Mutations In DNA Hybrids By Direct Electric Field Control", Proc. Natl. Acad. Sci. USA, vol. 94, No. 4, Feb. 1997, 1119-1123.

Southern, et al., "Analyzing and Comparing Nucleic Acid Sequences By Hybridization To Arrays of Oligonucleotides: Evaluation Using Experimental Models", Genomics, vol. 13, 1992, 1008-1017.

Strezoska, et al., "DNA Sequencing By Hybridization: 100 Bases Read By A Non-Gel Based Method", Proc. Natl. Acad. USA, vol. 88, Nov. 1991, 10089-10093.

Wallace, et al., "Hybridization Of Synthetic Oligodeoxyribonucleotides to Φ x 174 DNA: The Effect of Single Base Pair Mismatch", Nucleic Acids Research, vol. 6, No. 11, 1979, 3543-3557.

Washizu, "Electrostatic Manipulation Of Biological Objects", Journal of Electrostatics, vol. 25, 1990, 109-123.

Washizu, et al., "Electrostatic Manipulation Of DNA In Microfabricated Structures" IEEE Transactions On Industry Applications, vol. 26, No. 6, Nov./Dec. 1990, 1165-1172.

"Le Principe d l' Hybridization ", Biofutur. Le Mensuel Europeen de Biotechnology, Editions Scientifiques Elsevier, Paris, FR, vol. 1997, No. 166, Apr. 1997, XP004279767, p. 3. ISSN:0294-3508.

* cited by examiner

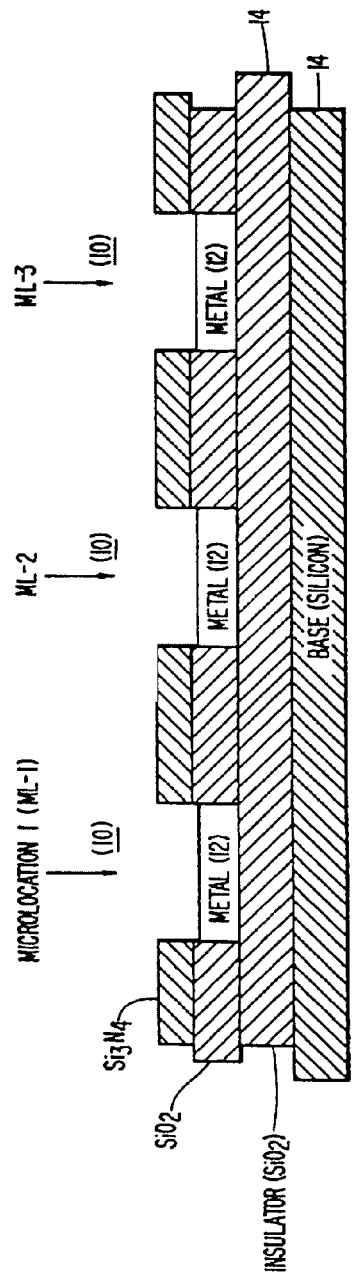
Fig. 1 Self-Addressable Microlocations
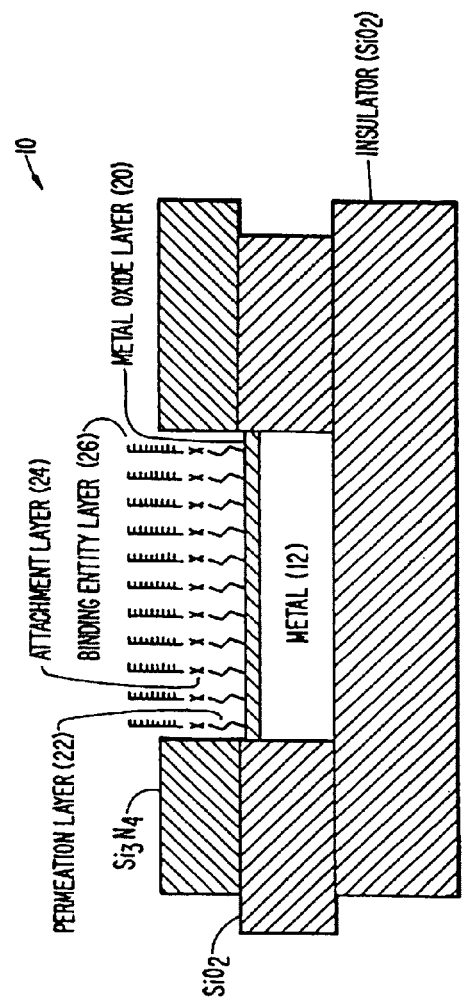
Fig. 2 Cross-section of a Microlocation

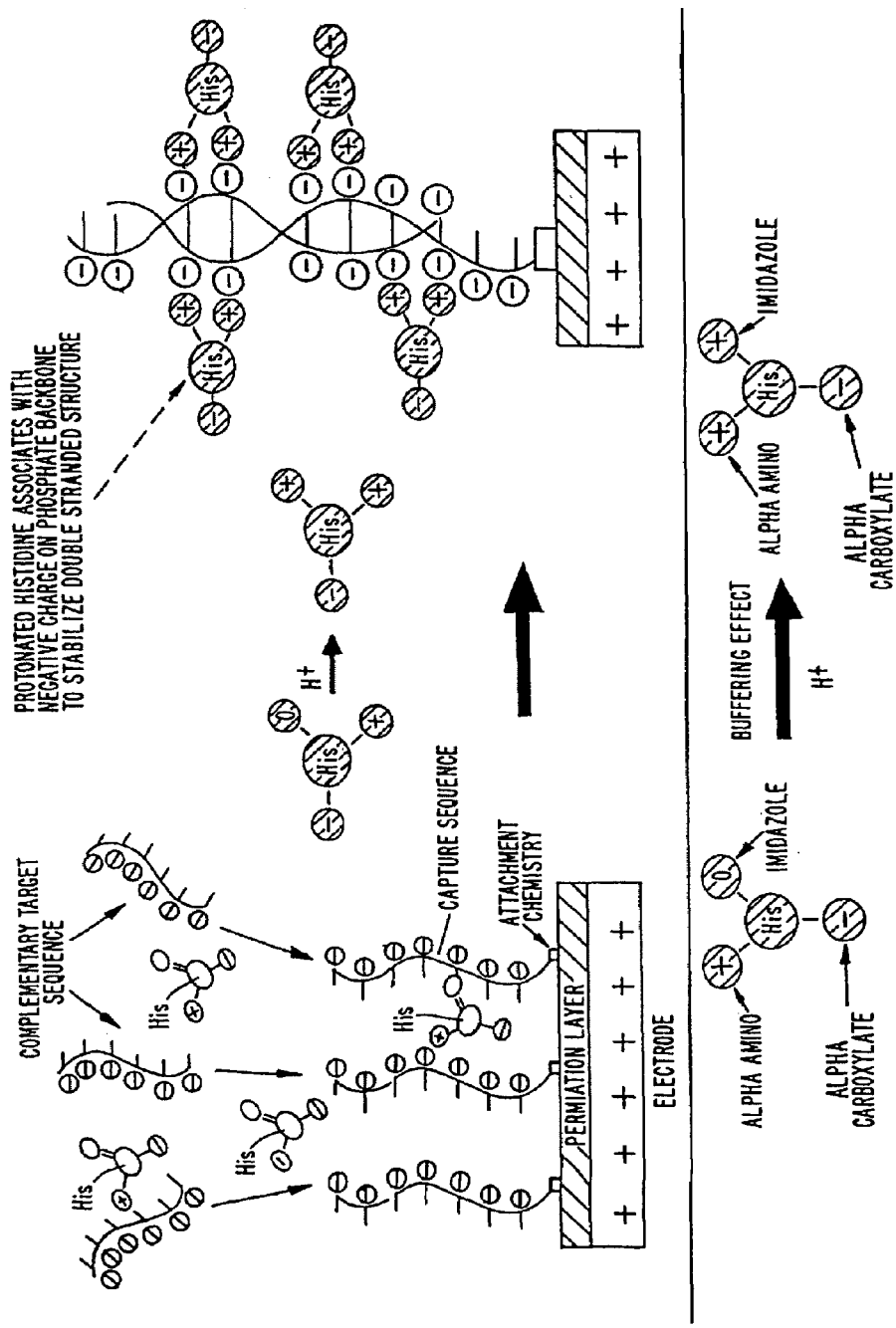
Fig. 3 Histidine Stabilization

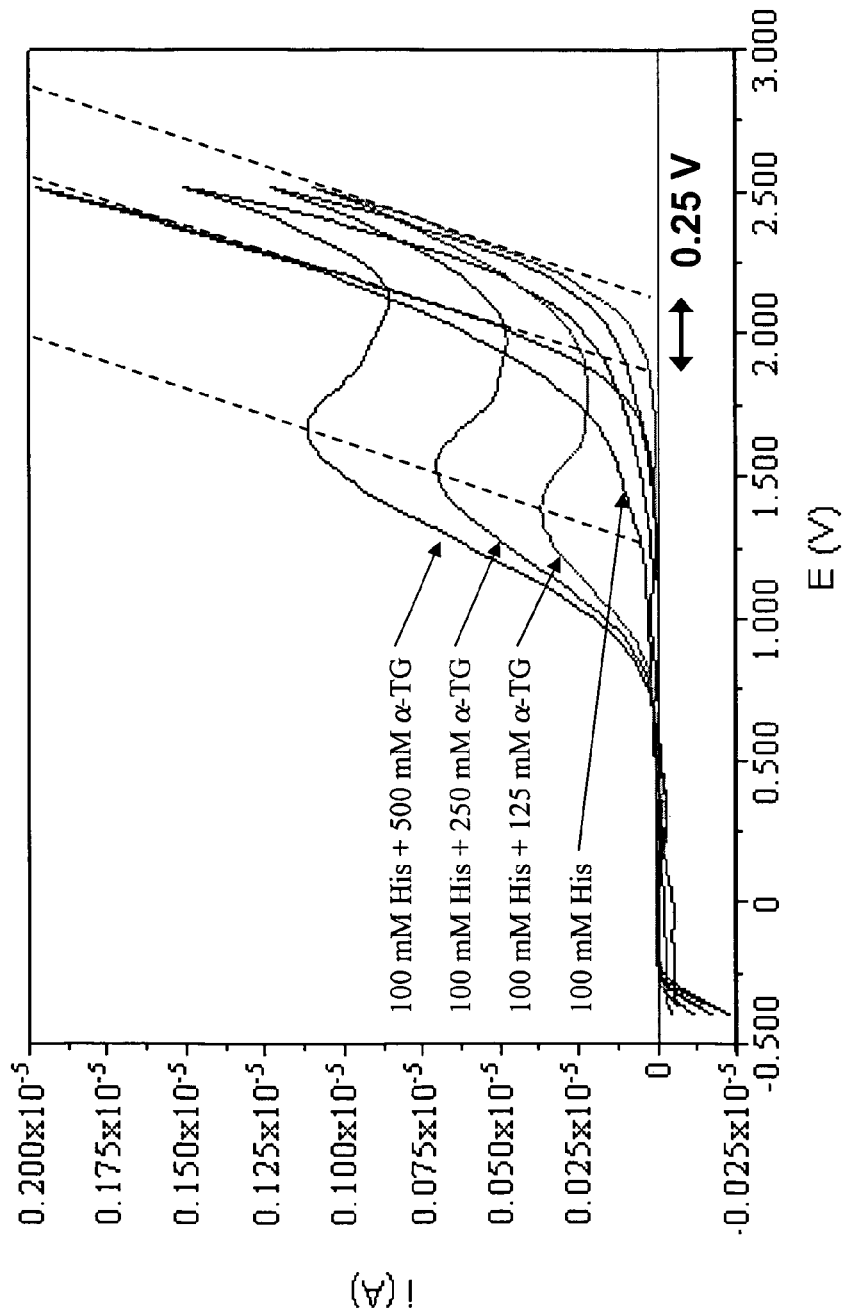
Fig. 4 Oxidation/Reduction Potential Sweeps

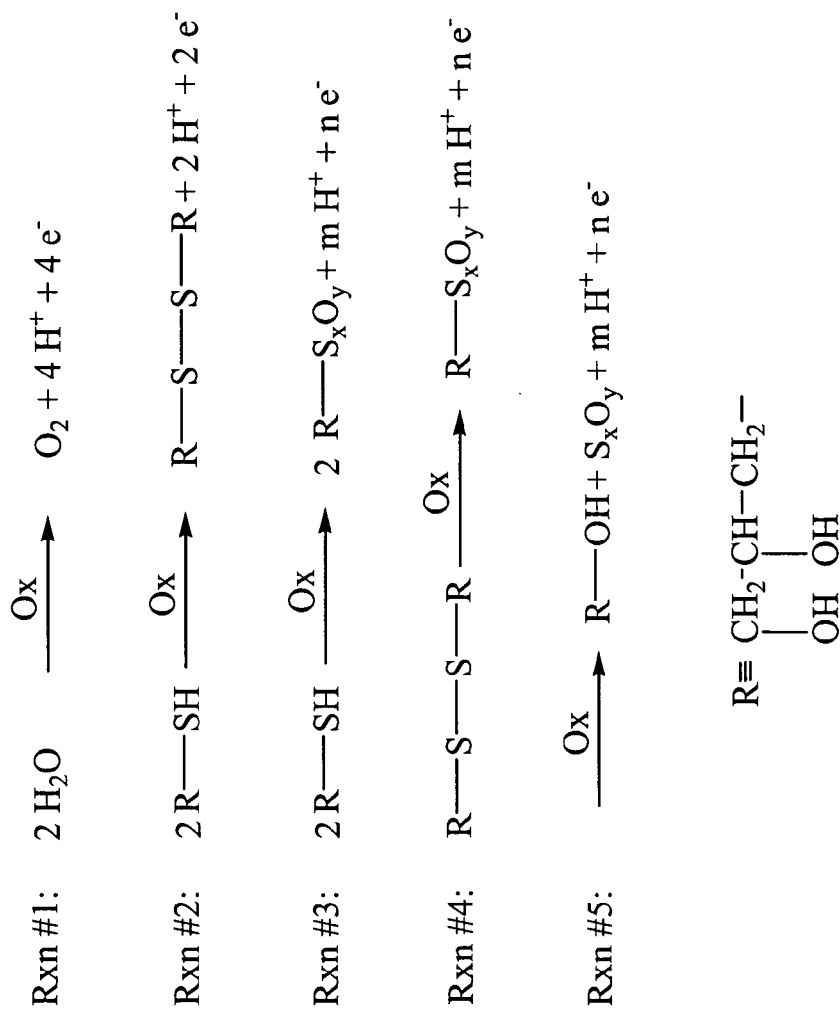
Fig. 5 Products of Water and α-Thioglycerol Oxidation

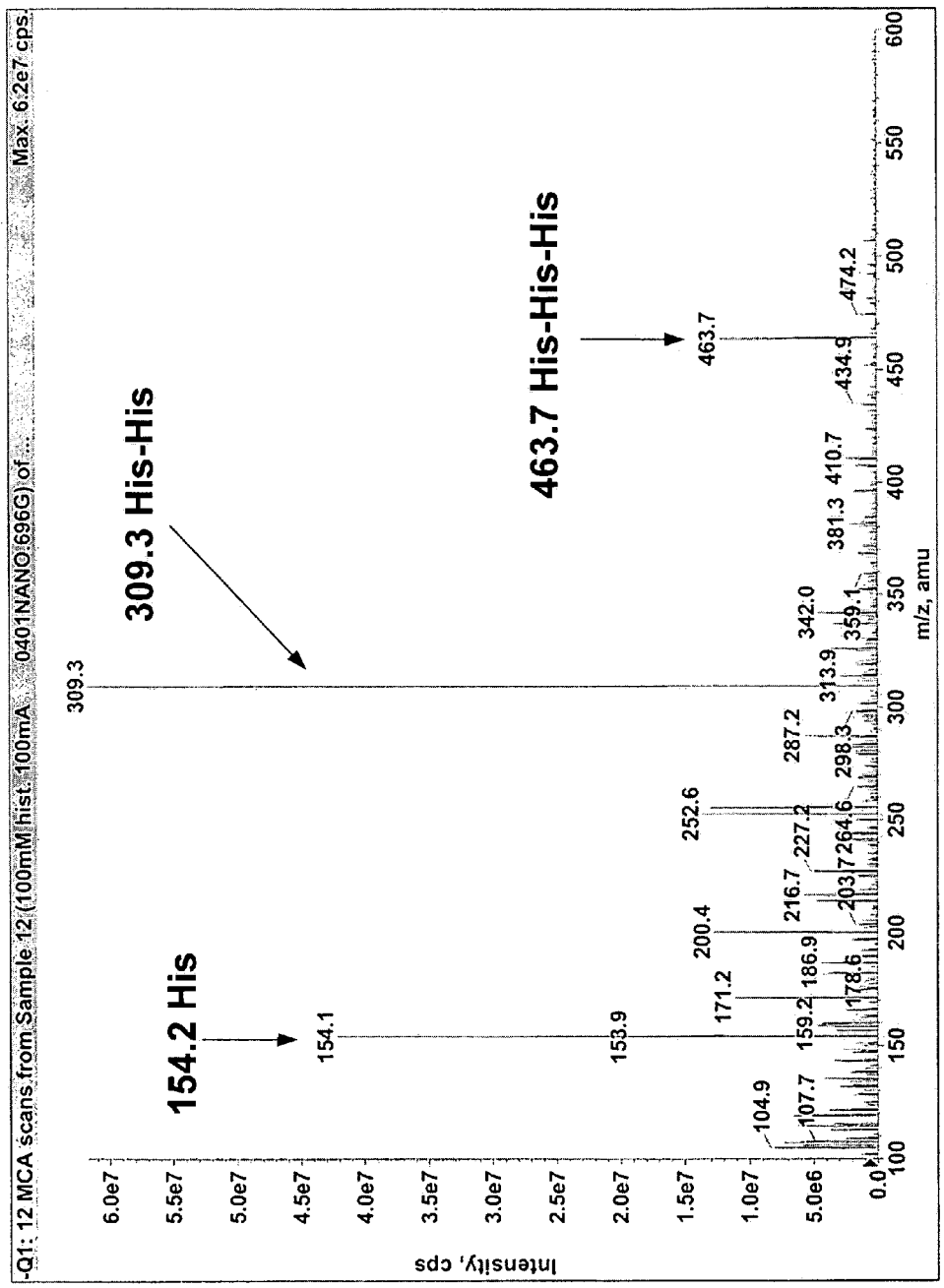
Fig. 6 Mass Spectrum of Electrolyzed Histidine

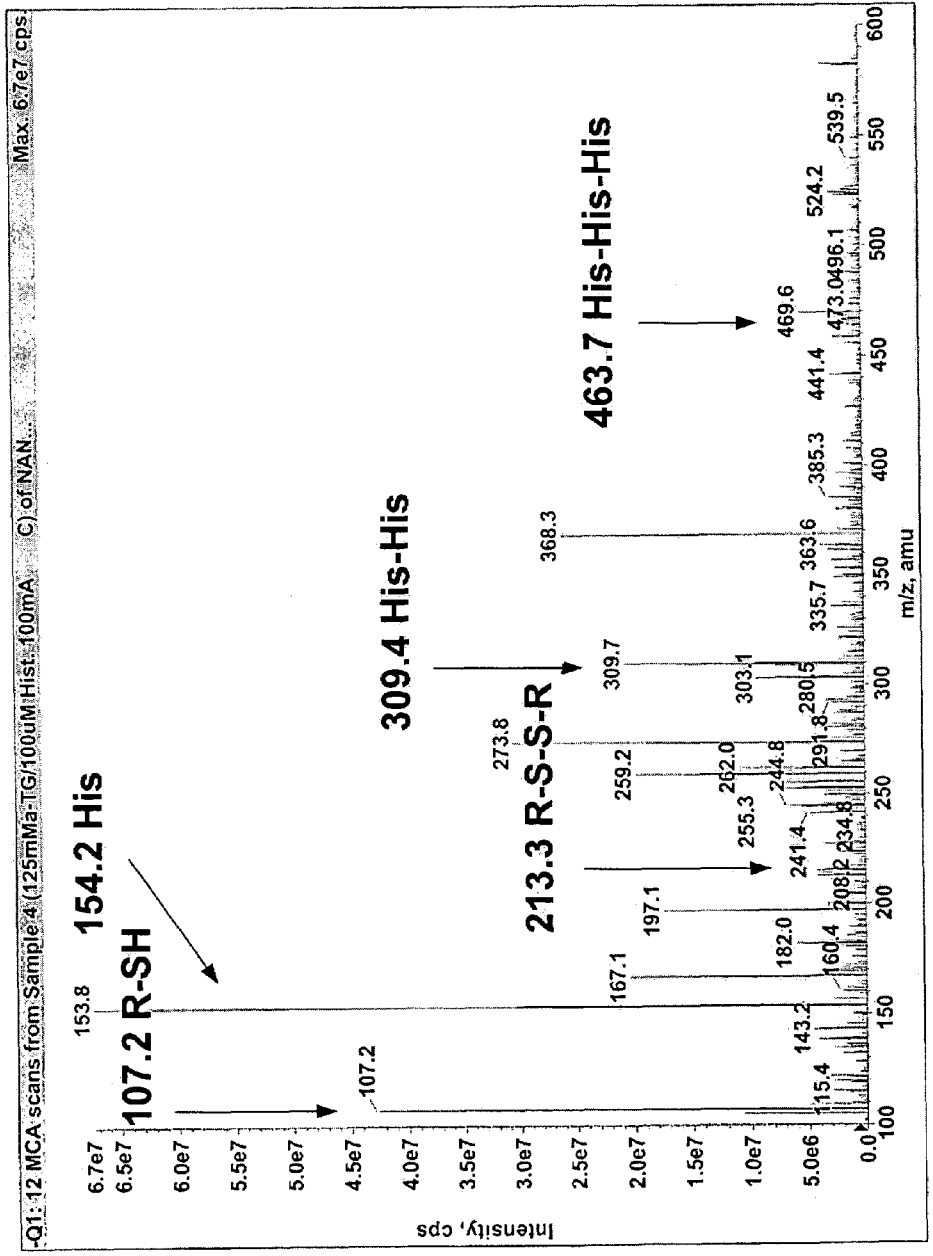
Fig. 7 Mass Spectrum of Electrolyzed α−TG/Histidine

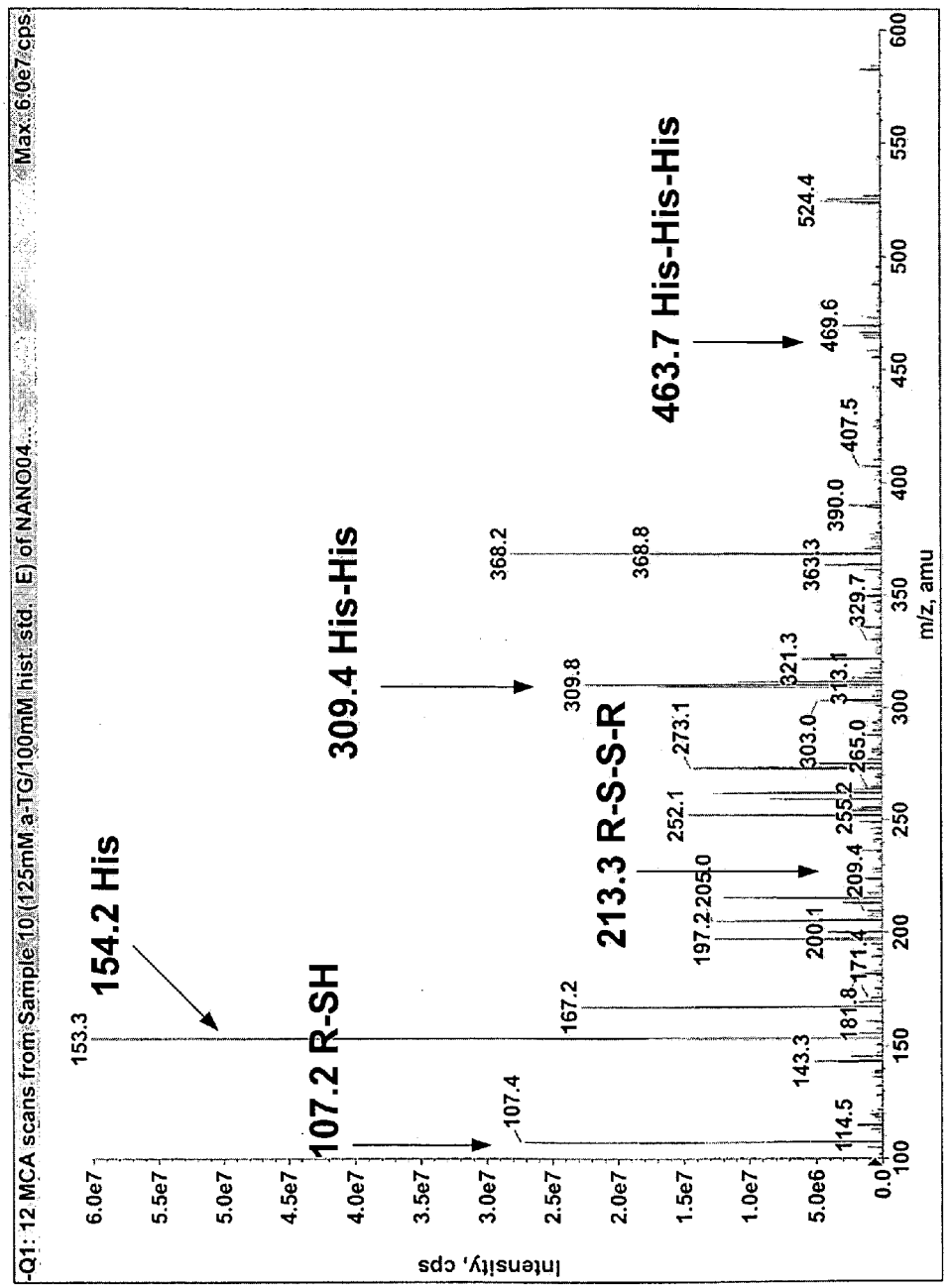
Fig. 8 Mass Spectrum of α-TG/Histidine

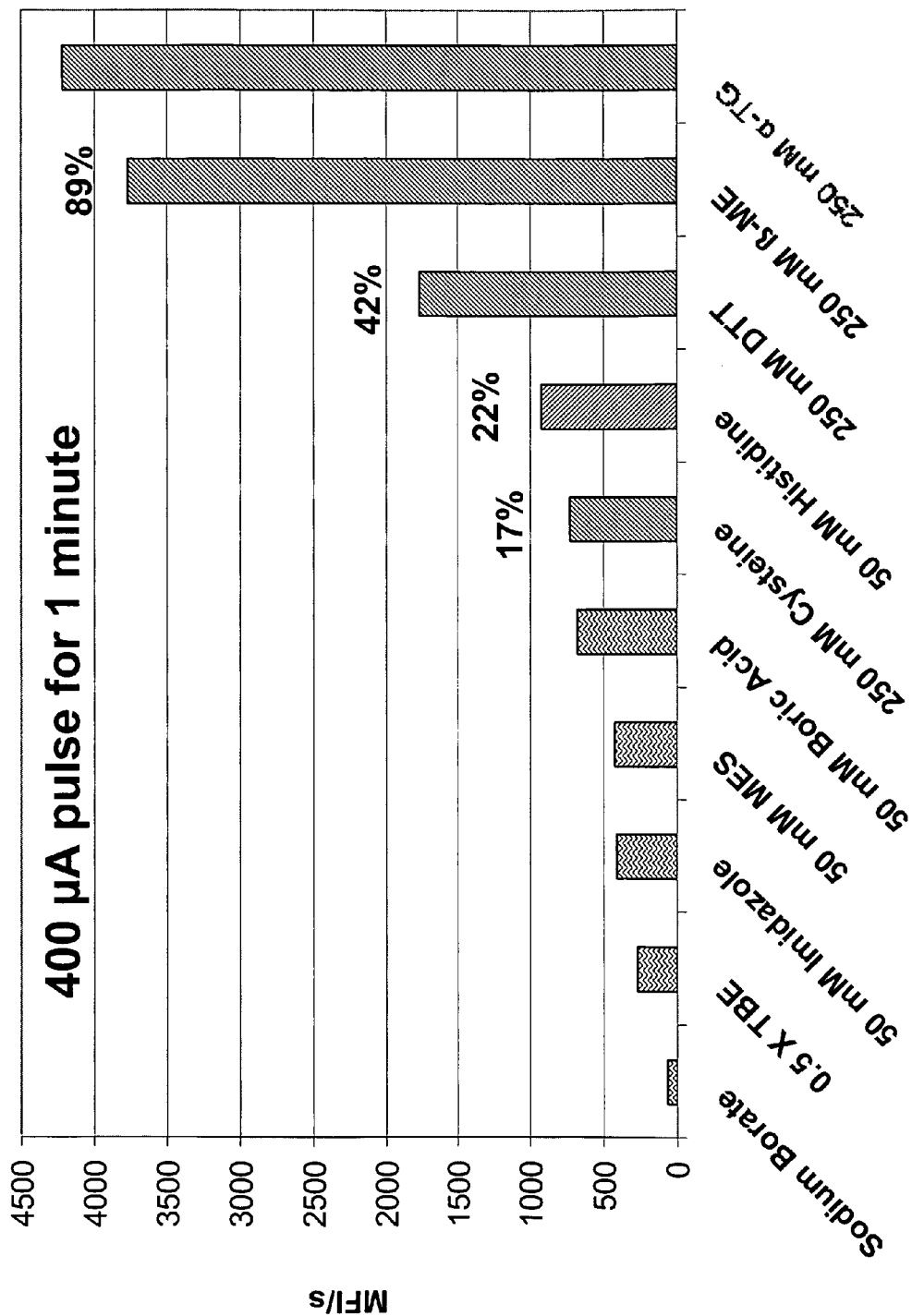
Fig. 9 CRD Signal Accumulation

METHODS AND MATERIALS FOR OPTIMIZATION OF ELECTRONIC TRANSPORTATION AND HYBRIDIZATION REACTIONS

This application claims the benefit of provisional U.S. Application Ser. No. 60/613,148, filed on Sep. 23, 2004, the entirety of which is hereby incorporated by reference in its entirety.

FIELD OF THE INVENTION

This invention relates to buffers and electrolytes and methods for their use in electronic devices adapted for medical diagnostic, biological, and other microfluidic applications. More particularly, it relates to buffers, electrolytes, and methods for their use with DNA transport and subsequent hybridization analysis carried out on microelectronic diagnostic devices.

BACKGROUND OF THE INVENTION

Recently, there has been increasing interest in devices that combine electronics and molecular mechanisms. These systems are able to perform a wide variety of functions that are advantageously used in molecular biology reactions, such as nucleic acid hybridizations, antibody/antigen reactions, clinical diagnostics, and biopolymer synthesis. These systems include any electrode device. The system may have a single electrode or multiple electrodes. One such system is disclosed in "ACTIVE PROGRAMMABLE ELECTRONIC DEVICES FOR MOLECULAR BIOLOGICAL ANALYSIS AND DIAGNOSTICS," Ser. No. 08/146,504, filed Nov. 1, 1993, now issued as U.S. Pat. No. 5,605,662, which is expressly incorporated herein by reference in its entirety.

Electrode devices utilize buffers and electrolytes for their operation. A buffer has been defined as a chemical solution that is resistant to change in pH on the addition of acid or alkali. See., e.g., Dictionary of Biotechnology, Second Edition, James Coombs, Stockton Press. As stated there, "traditionally, buffers based on inorganic salts (phosphate, carbonate) and organic acid salts (acetate, citrate, succinate, glycine, maleate, barbiturates, etc.) were used in biological experiments."

It is the object of this invention to discover buffers and electrolytes that are advantageously used in molecular electronic devices that perform transport, hybridizations, reactions, diagnostics, and/or synthesis.

SUMMARY OF THE INVENTION

The following inventions relate to our discoveries concerning the various parameters, electrolytes (buffers), and other conditions that improve or optimize the speed of transport of charged biomolecules (e.g., DNA, RNA, etc.), the efficiency of hybridization reactions, and the overall hybridization specificity in microelectronic chips and devices. In particular, this invention relates to the discovery that low conductance zwitterionic buffers containing a reducing agent provide optimal conditions for both rapid DNA transport and efficient hybridization reactions.

The method of the present invention relates to transporting and hybridizing nucleic acids in an electrode device. A low conductivity, zwitterionic buffer containing a reducing agent is provided to the electrode device. The nucleic acid is then electrophoretically transported to a location of the electrode device by applying a current and voltage to the electrode at the location. The nucleic acid can then be hybridized to a probe located at the electrode, whereby the local pH above the microlocation is below the pH of the buffer at its isoelectric point. Alternatively, the nucleic acid can be coupled to a permeation layer associated with the electrode at the location.

In another embodiment of the present invention, the method relates to the transport and hybridization of nucleic acids on an electrode device, wherein the device has a location having a nucleic acid probe. A low conductivity, zwitterionic buffer containing a reducing agent is applied to the electrode device. A target nucleic acid is then applied to the device. The target nucleic acid is then concentrated to the location by applying current and potential to the device. Once at the location, the target nucleic acid hybridizes with the nucleic acid probe.

In another embodiment of the present invention, the method relates to electronically enhancing hybridization of a DNA analyte to a single stranded capture DNA at a location in an electric field at a positively biased location on an electrode device. A buffer containing a reducing agent and a low conductance, zwitterionic molecule is applied to the device. Current is then applied to the location in an amount sufficient to produce an electric field at the location, wherein the location is positively biased relative to the DNA analyte. As a result, the DNA analyte is transported to the location. Once at the location, the DNA analyte is hybridized to the single stranded capture DNA, wherein positively charged buffer molecules at the location stabilize the hybridization.

In another embodiment of the present invention, the method relates to transporting a nucleic acid in an electrode device. A double-stranded nucleic acid having a first and a second strand is added to a low conductivity, zwitterionic buffer with a reducing agent. The double-stranded nucleic acid is then denatured by the low conductivity, zwitterionic buffer containing a reducing agent into the first and second single strands. The nucleic acids are then loaded onto the device in the low conductivity, zwitterionic buffer containing a reducing agent. An electrode of the electrode device is also provided with a capture sequence, wherein the capture sequence is complementary to the first strand of the double-stranded nucleic acid. Current and voltage are then applied to the electrode at a temperature of less than about 30° C. in order to effect electrophoretic transportation of the first strand towards the electrode. Subsequently, the first strand of the nucleic acid hybridizes with the capture sequence associated with the electrode. In alternative embodiments, the current and voltage are applied to the electrode at a temperature of less than about 28° C., alternatively less than about 25° C., alternatively less than about 23° C., alternatively less than about 20° C., alternatively less than about 18° C., alternatively less than about 15° C., alternatively less than about 10° C.

In another embodiment of the present invention, the method of the present invention relates to transporting and hybridizing nucleic acids in an electrode device. A low conductivity buffer containing a reducing agent is provided to the electrode device. The nucleic acid is then electrophoretically transported to a location of the electrode device by applying a current and voltage to the electrode at the location. The nucleic acid can then be hybridized to a probe located at the electrode. Alternatively, the nucleic acid can be coupled to a permeation layer associated with the electrode at the location.

In all of the various methods described above, the reducing agent may be α-thioglycerol, dithiotreitol, β-mercaptoethanol, cysteine, or combinations thereof. The concentration of the reducing agent should be sufficient to reduce bubbling at the electrode so as not to interfere with the hybridization of the DNA. The concentration of the reducing agent may be about 25-700 mM, alternatively about 25-500 mM, alternatively about 25 mM, alternatively about 50 mM, alternatively about 100 mM, alternatively about 125 mM, alternatively about 150 mM, alternatively about 250 mM, alternatively about 500 mM.

In all of the various methods described above, the low conductance, zwitterionic buffer may contain histidine (either D- or L-histidine), γ-aminobutyric acid (GABA), alanine, lysine, glutamic acid, any other naturally occurring or synthetic zwitterion, or any combinations thereof.

BRIEF DESCRIPTION OF THE FIGURES

FIG. 1. is the cross-section of three self-addressable microlocations.

FIG. 2 is the cross-section of a microlocation.

FIG. 3 shows a graphical representation of histidine stabilization of hybrids in the electronic hybridization process.

FIG. 4 shows a graph of oxidation/reduction potential sweeps.

FIG. 5 shows the products of water and α-thioglycerol oxidation.

FIG. 6 is a mass spectrum of an electrolyzed histidine buffer.

FIG. 7 is a mass spectrum of an electrolyzed histidine buffer containing α-thioglycerol.

FIG. 8 is a mass spectrum of a histidine buffer containing α-thioglycerol.

FIG. 9 is a graph of signal accumulation on an electrode device using different buffers.

DETAILED DESCRIPTION OF THE INVENTION

The devices and the related methodologies of this invention allow molecular biology and diagnostic reactions to be carried out under "complete electronic control." The meaning of "electronic control" as referred to in this invention goes beyond the conventional connotation of the term. Most conventional electronic devices, instruments, and detector systems are always at some level under electronic control. The electronic devices of this invention are not only under conventional electronic control, but more importantly, they also provide further direct electronic control over the physical aspects of carrying out molecular biological and diagnostic reactions. This invention provides an electronic device with an electrode. The electronic device may have a single electrode or multiple electrodes. For instance, the electronic device may have 1, 4, 8, 6, 16, 25, 36, 100, 400, 1000, or 10,000 electrodes.

One such device is the APEX system. The details of the APEX device are in U.S. application Ser. No. 08/146,504, now issued as U.S. Pat. No. 5,605,662, which is referred to and incorporated by reference above. Briefly, FIG. 1 shows a basic design of self-addressable microlocations fabricated using microlithographic techniques. The three microlocations (10) (ML-1, ML-2, ML-3) are formed on the surface of metal sites (12) that have been deposited on an insulator layer/base material. The metal sites (12) serve as the underlying microelectrode structures (10). An insulator material separates the metal sites (12) from each other. Insulator materials include, but are not limited to, silicon dioxide, glass, resist, rubber, plastic, or ceramic materials.

FIG. 2 shows the basic features of an individual microlocation (10) formed on a microlithographically produced metal site (12). The addressable microlocation is formed on the electrode/metal site (12), and incorporates a permeation layer (22). The electrode/metal site may include platinum, platinum-silicide, carbon, and any other suitable material known to one of ordinary skill in the art. The permeation layer provides spacing between the metal surface and the probes or specific binding entities and allows for solvent molecules, small counter-ions, and gases to freely pass to and from the surface of the electrode. Probes or specific binding entities can couple to attachment sites in the permeation layer. Details of various permeation layers can be found in U.S. application Ser. Nos. 10/014,895, filed Dec. 10, 2001; 09/464,670, filed Dec. 15, 1999, now issued as U.S. Pat. No. 6,303,082; and 09/922,349, filed Aug. 3, 2001, all of which are herein expressly incorporated by reference in their entirety.

After the initial fabrication of the basic microelectronic structure, the device is able to self-direct the addressing of each specific microlocation with specific binding entities or capture probes. Thus, the devices and methods of this invention can be combined into an instrument system that allows addressing of an APEX chip device with any DNA or RNA probe, or any other ligand. Such a system allows "make your own chip" products and applications. Such products and applications would be useful to many researchers and end users for clinical diagnostic, molecular biology, functional genomic and drug discovery applications. The self-addressed device is subsequently able to actively carry out individual multi-step and combinatorial reactions at any of its microlocations. The device is able to carry out multiplex reactions, but with the important advantage that each reaction occurs at the equivalent of a truly independent test site. The device is able to electronically direct and control the rapid movement and concentration of analytes and reactants to or from any of its microlocations. The ability of the device to electronically control the dynamic aspects of various reactions provides a number of new mechanisms and important advantages and improvements.

There are various physical parameters that relate to the electrophoretic transport of DNA and other charged analytes in various types of electrolyte/buffer solutions. Certain of the devices, e.g., the APEX device as described in Ser. No. 08/146,504, referenced above, are primarily DC (direct current) electrical devices. Electrophoretic transport of charged molecules occurs between oppositely (±) biased microlocations on the device surface.

APEX type devices produce significant net direct current (DC) flow when a voltage is applied, which is recognized as "the signature of electrophoresis." In electrophoresis, the migration of ions or charged particles is produced by electrical forces along the direction of the electric field gradient, and the relationship of current and voltage are important to this technology. The electrophoretic migration shows itself macroscopically as the conduction of electric current in a solution under the influence of an applied voltage and follows Ohm's law.

$V = R \times I$

V is the electric potential

R is the electric resistance of the electrolyte [$V \times A^{-1} = R\ (\Omega)$]

I is the electric current [A].

The resistance of the solution is the reciprocal of the conductance, which can be measured by a conductometer. The conductance depends mainly on the ionic species of the buffer/electrolytes and their concentration; therefore these parameters are very important for electric field related molecular biology technology. The basic current/voltage relationships are essentially the same for the APEX technology as for any other electrophoretic system, although the electric fields produced are in truly microscopic environments.

There are unique features of the APEX system regarding the various ways of sourcing the current and voltage, and how the current and voltage scenarios have been found to improve the performance of our systems. In particular, various DC pulsing procedures (linear and logarithmic gradients) appear to provide improved hybridization stringency.

The details of complexity reduction devices are in U.S. application Ser. No. 08/709,358, now issued as U.S. Pat. No. 6,129,828, which is hereby expressly incorporated by reference in its entirety.

Electrophoretic Transport Versus Ionic Strength

It is well established in the field of electrophoresis that there is a logarithmic decrease in the mobility of the charged analyte species (proteins, DNA, etc.), which is inversely proportional to the square root of the ionic strength of the electrolyte solution (see page 83 and FIG. 3.16 in "Capillary Electrophoresis: Principles and Practice", R. Kuhn and S. Hoffstetter, Springer-Verlag, 1993). At any given constant electric field strength, as the electrolyte concentration decreases relative to the analyte species (protein, DNA, etc.), the analyte will be transported at a faster rate. Similar results demonstrating this effect for a danyslated amino acid have been shown by J. J. Issaq et. al., Chromatographia Vol.32, #3/4, August 1991, pages 155 to 161 (see in particular FIG. 3 on page 157). Results demonstrating this effect for DNA in different electrolyte solutions has been shown in P. D. Ross and R. L. Scruggs, Biopolymers Vol. 2, pages 231 to 236, 1964 (see in particular FIG. 1, page 232).

Ionic Strength/Conductance Relationship

For those non-buffering electrolytes (sodium chloride, potassium chloride, etc.) that involve completely dissociated anion and cation species in solution ($Na^+ \leftrightarrows Cl^-$, $K^+ \leftrightarrows Cl^-$, etc.), the ionic strength and conductance are equivalent, i.e., the conductance will usually be proportional to the ionic strength. For those buffering electrolytes (phosphate, acetate, citrate, succinate, etc.) that are in their dissociated states (example: $2\ Na^+ \leftrightarrows PO_4^{-2}$), the ionic strength and conductance will usually be equivalent, i.e., conductance is proportional to the ionic strength. For those buffering electrolytes (Good Buffers—MOPS, HEPES, TAPS, Tricine, Bicine, Amino Acid Buffers, Ampholytes, etc.) that can have a zwitterionic species (no net charge at their pI), the conductance will decrease by approximately a factor of 10 for every pH unit difference between the isoelectric point (pI) and the (pKa). For example, an amino acid in its zwitterionic state ($^-OOC$—$CH(R)$—$NH_3^+$) will have a conductance value that will be approximately 1000 fold lower than when the "amino acid moiety" has a full net positive charge ($HOOC$—$CH(R)$—$NH_2^+ X^-$), or a full negative charge ($Y^{+-}OOC$—$CH(R)$—$NH_2$). Thus, a formal negative or positive charge develops on the amino acid moiety as it moves away from its pI, and the conductivity and ionic strength will begin to correlate. When at or near the pI, however, the conductance will be much lower than is expected for that given ionic strength or concentration. When used at or near their pI's, electrophoresis texts refer to the Good Buffers and amino acid buffers as having "low conductance's at high ionic strength or concentration" (see page 88 of Capillary Electrophoresis: Principles and Practice", R. Kuhn and S. Hoffstetter, Springer—Verlag, 1993). A commonly used electrophoresis buffer "Tris-Borate" actually has a significantly lower conductivity than would be expected from its ionic strength or concentration. This may be due to the "tris cation" and "borate anion" forming a relatively stable zwitterionic complex in solution. The conductivity of a 100 mM Tris-Borate solution was determined to be 694 μS/cm, which is approximately 20 times lower than would be expected from its ionic strength, and is roughly equivalent to a 5 mM sodium phosphate or sodium chloride solution. Table 1 shows conductivity measurements of a number of transport buffers.

TABLE 1

| Solution/Buffer | Measurement 1 | Measurement 2 | Measurement 3 | Average/Std. Deviation |
|---|---|---|---|---|
| 10 mM MgCl$_2$ | 1.95 mS/cm | 2.02 mS/cm | 2.13 mS/cm | 2.03 +/− 0.09 mS/cm |
| 1 mM MgCl$_2$ | 174 μS/cm | 208 μS/cm | 177 μS/cm | 186 +/− 18.8 μS/cm |
| 0.1 mM MgCl$_2$ | 16.9 μS/cm | 16.7 μS/cm | 18.3 μS/cm | 17.3 +/− 0.87 μS/cm |
| 10 mM NaCl | 1.07 mS/cm | 1.10 mS/cm | 1.18 mS/cm | 1.12 +/− 0.057 mS/cm |
| 1 mM NaCl | 112 μS/cm | 115 μS/cm | 111 μS/cm | 112.7 +/− 2.08 μS/cm |
| 0.1 mM NaCl | 8.80 μS/cm | 8.98 μS/cm | 10.5 μS/cm | 9.43 +/− 0.93 μS/cm |
| 20 mM NaPO$_4$ | 2.90 mS/cm | 2.79 mS/cm | 3.00 mS/cm | 2.90 +/− 0.11 mS/cm |
| 10 mM NaPO$_4$ | 1.40 mS/cm | 1.44 mS/cm | 1.48 mS/cm | 1.44 +/− 0.04 mS/cm |
| 1 mM NaPO$_4$ | 122 μS/cm | 128 μS/cm | 136 μS/cm | 128.7 +/− 7.0 μS/cm |
| 50 mM TRIS | 3.50 mS/cm | 3.14 mS/cm | 3.40 mS/cm | 3.35 +/− 0.19 mS/cm |
| 10 mM TRIS | 572 μS/cm | 562 μS/cm | 583 μS/cm | 572 +/− 10.5 μS/cm |
| 250 mM HEPES | 141 μS/cm | 144 μS/cm | 158 μS/cm | 147.6 +/− 9.07 μS/cm |
| 25 mM HEPES | 9.16 μS/cm | 9.44 μS/cm | 10.5 μS/cm | 9.7 +/− 0.71 μS/cm |
| 3.3 mM NaCitrate | 964 μS/cm | 964 μS/cm | 1.03 mS/cm | 986 +/− 38.1 μS/cm |
| 5 mM NaSuccinate | 1.05 mS/cm | 960 μS/cm | 1.01 mS/cm | 1.01 +/− 0.045 mS/cm |
| 5 mM NaOxalate | 1.02 mS/cm | 1.03 mS/cm | 1.12 mS/cm | 1.06 +/− 0.055 mS/cm |
| 10 mM NaAcetate | 901 μS/cm | 917 μS/cm | 983 μS/cm | 934 +/− 43.5 μS/cm |
| 250 mM Cysteine | 27.4 μS/cm | 17.3 μS/cm | 23.5 μS/cm | 22.7 +/− 5.09 μS/cm |
| Milli-Q water | <0.5 μS/cm | | | Detection limit of 0.1 cell too low |

Zwitterionic Buffers/Conductance/Transport Rate

Certain advantages exist regarding the rate or speed of electrophoretic transport of DNA when using Zwitterionic buffers (Good buffers, amino acid buffers), or the Tris-Borate buffer at or near their pI's. These advantages include: 1) zwitterionic buffers can be used at relatively high concentrations to increase buffering capacity; 2) the conductance of zwitterionic buffers is significantly lower than other types of buffers at the same concentration, and 3) zwitterionic buffers have higher electrophoretic transport rates for the analyte of interest (e.g., DNA, RNA).

Zwitterionic Buffer Capacity at the Isoelectric Point (pI)

Amino acid buffers have buffer properties at their pI's. While a given amino acid may or may not have its "highest buffering capacity" at its pI, it will have some degree of buffering capacity. Buffer capacity decreases by a factor of 10 for every pH unit difference between the pI and the pKa; those amino acids with three ionizable groups (histidine, cysteine, lysine, glutamic acid, aspartic acid, etc.) generally have higher buffering capacities at their pI's than those amino acids with only two ionizable groups (glycine, alanine, leucine, etc.). For example, histidine (pI=7.47), lysine (pI=9.74), and glutamic acid (pI=3.22), all have relatively good buffering capacity at their pI's relative to alanine or glycine, which have relatively low buffering capacities at their pI's (see A. L. Lehninger, Biochemistry, 2ed, Worth Publishers, New York, 1975; in particular FIGS. 4-8 on page 79, and FIGS. 4-9 on page 80). Histidine has been proposed as a buffer for use in gel electrophoresis, see, e.g., U.S. Pat. No. 4,936,963, but hybridization is not performed in such systems. Cysteine is in a more intermediate position, with regard to buffering capacity. The pI of cysteine is 5.02, the pKa for the α-carboxyl group is 1.71, the pKa for the sulfhydryl is 8.33, and the pKa for α amino group is 10.78. An acid/base titration curve of 250 mM cysteine, shows that cysteine has a better "buffering capacity" at ~pH 5 than a 20 mM sodium phosphate. In the pH 4 to 6 range, the buffering capacity of cysteine is significantly better than 20 mM sodium phosphate, particularly at the higher pH. In these pH ranges, however, the conductance of the 250 mM cysteine solution is very low ~23 µS/cm, compared to 20 mM sodium phosphate, which has a value of ~2.9 mS/cm (a factor of 100 times greater). Low conductance zwitterionic buffers suitable for APEX devices have been disclosed in U.S. application Ser. Nos. 09/986,065, filed Dec. 5, 1997, now issued as U.S. Pat. No. 6,051,380; 09/444,539, filed Nov. 22, 1999, now issued as U.S. Pat. No. 6,518,022; 10/170,172, filed Jun. 11, 2002; and 08/708,262, filed Sep. 6, 1996, now abandoned, all of which are herein expressly incorporated by reference in their entirety.

Several electrophoretic techniques developed over 20 years ago are based on the ability to separate proteins in zwitterionic buffers "at their pI's," these techniques are called Isoelectrophoresis, Isotachophoresis, and Electrofocusing (see chapters 3 and 4 in "Gel Electrophoresis of Proteins: A Practical Approach" Edited by B. D. Hames & D. Rickwood, IRL Press 1981). Various amino acid buffers and Good buffers were used for these applications, all at their pI's (see Table 2, page 168 of the above reference).

DNA Transport in Low Ionic Strength and Low Conductance Buffers

A series of fluorescent checkerboard experiments were carried out using 2.5% agarose coated 5580 chips and the ByTr-RCA5 fluorescent probe. Rapid (6 second) checkerboard addressing was achieved in all of the following systems: (1) 250 mM HEPES (low conductance), (2) 10 µM sodium succinate, (3) 10 µM sodium citrate, and (4) distilled water. While some types of low conductance or low ionic strength solutions may have somewhat better characteristics, checkerboard addressing and rapid DNA transport (6 to 12 second DNA accumulation on an 80 µm pad) were achieved using all of these systems. Additionally, DNA addressing APEX chips in distilled water is possible because the DNA, which is itself a polyanion, is the electrolyte present in the bulk solution that provides the conductance.

Relationship of Electrophoretic Transport Rate and the Cation/Anion Species

In addition to the fact that the mobility of the charged analyte species (DNA, proteins, etc.) is related to the ionic strength of the electrolyte solution, the mobility is also greatly influenced by the nature of the cationic and anionic species in the electrolyte solution (see pp 89 of "Capillary Electrophoresis: Principles and Practice" reference). This particular point is demonstrated for DNA transport in the above-referenced Biopolymers, Vol. 2, pp. 231-236, 1964 reference. FIG. 1 on page 232 of this reference shows the change in DNA mobility when using electrolytes with different univalent anions ($Li^+>Na^+>K^+>TMA^+$) at the same ionic strength. Basically, different cations can have different association constants with the DNA phosphate groups, and/or change the hydration spheres around the DNA molecules, which leads to a change in their transport rate.

The instant invention also relates to our discoveries concerning the various parameters, electrolytes (buffers), and other conditions that improve or optimize the speed of DNA transport, the efficiency of DNA hybridization reactions, and the overall hybridization specificity in electric field molecular biology devices, especially APEX microelectronic chips and devices. In particular, this invention relates to our discovery that low conductance zwitterionic buffer solutions containing a reducing agent provides good conditions for both rapid electrophoretic DNA transport and efficient hybridization reactions.

The zwitterionic buffer component can be any molecule that can have a zwitterionic species (no net charge at its pD). In one embodiment, the zwitterionic species is an amino acid. The amino acid can include, but is not limited to, histidine, alanine, arginine, glutamic acid, lysine, γ-aminobutyric acid (GABA), etc. In a preferred embodiment, the amino acid is Histidine. The concentration of histidine can range from 10-200 mM, alternatively 10-100 mM, alternatively 50-100 mM, alternatively about 50 mM, alternatively about 100 mM, at or near the pI (isoelectric point ~7.47). The concentration of histidine in the buffer will depend on the salt composition and can be determined by one of ordinary skill in the art.

The advantages of the histidine buffer is particularly important for the APEX chip type devices. These particular devices (as opposed to the micromachined type devices) have limitations as to the amount of current and voltages that can be applied. This limitation makes it difficult to achieve both rapid transport and efficient hybridization using the same buffer system.

In one embodiment, DNA transport was carried out in a low conductance buffer (cysteine or alanine) where the limited current/voltage still produced rapid transport. Under these conditions, the DNA accumulated at the test site, but did not hybridize as efficiently. After transport in these low conductance buffers, the solution was changed to a high salt buffer (>100 mM sodium chloride or sodium phosphate), which then produced an efficient hybridization at the test site.

Table 2 shows the results for a series of experiments that correlate the parameters of buffer capacity, pH, and the conductivity, with DNA accumulation and hybridization sensitivity (efficiency) using the APEX chip device.

TABLE 2

| Solution | Buffer Capacity pH 4-10 | | pH at pI | Conductivity (μS) | Relative DNA Transport Rate | SA-Biotin T12 Sensitivity | Hybridization Sensitivity of DNA |
|---|---|---|---|---|---|---|---|
| β-Alanine | $pK_1$ - 3.6<br>$pK_2$ - 10.2 | + | 7.3 | 10.0 | +++++<br>(fastest) | $3 \times 10^6$ | |
| Taurine | $pK_1$ - 1.5<br>$pK_2$ - 8.7 | +/− | 4.6 | 4.5 | ++++ | $>7.5 \times 10^{10}$ | |
| Cysteine | $pK_1$ - 1.7<br>$pK_2$ - 8.3<br>$pK_3$ - 10.8 | +/− | 5.2 | 25.0 | ++++ | $3 \times 10^7$ | $7.5 \times 10^{10}$ |
| Histidine | $pK_1$ - 1.8<br>$pK_2$ - 6.0<br>$pK_3$ - 9.0 | +++ | 7.6 | 212.0<br>(172.0 hi purity) | +++ | $3 \times 10^6$ | $3 \times 10^6$ |
| Lysine | $pK_1$ - 2.2<br>$pK_2$ - 8.9<br>$pK_3$ - 10.3 | ++ | 9.6 | 477.0 | ++ | $>7.5 \times 10^{10}$ | |
| $NaPO_4$ | Complex | + | 7.4[1] | 1,400.0 | +<br>(slowest) | | |

[1] 20 mM $NaPO_4$ adjusted to pH 7.4.

Table 2 clearly shows the correlation of DNA transport (accumulation) with low conductivity (β-alanine, taurine, cysteine, histidine). The table also shows good sensitivity for the streptavidin/biotin probe affinity reaction using β-alanine, cysteine, and histidine. As reflected in the sensitivity data in Table 2, histidine provides over four orders of magnitude better hybridization efficiency then either cysteine or other buffers, such as 20 mM $NaPO_4$. The improvement relative to cysteine is at least a factor of 10, alternatively a factor of $10^2$, and alternatively at least a factor of $10^4$. Histidine was found to provide both good transport and good DNA/DNA hybridization efficiency.

Histidine Mechanism of Action

During the transport and addressing procedures for DNA concentration and hybridization, the pH immediately above the positively biased electrode is found to be lowered, in a buffer dependent fashion. In separate experiments, it was observed for passive hybridization at acidic pH that histidine can facilitate hybridization when possessing a net positive charge but not when neutral. The ability of these histidine and associated buffers to facilitate electronic hybridization is linked to four important properties: (1) the ability to maintain target DNA in a relatively denatured state, (2) the ability to facilitate electric field concentration of DNA, (3) the ability to buffer acidic conditions present at the positively biased microlocation, (4) the ability to acquire a net positive charge capable of shielding or diminishing repulsion between the DNA phosphodiester backbone stabilizing the double-stranded structure. FIG. 3 shows the possible mechanism for histidine stabilization of DNA structures.

Basically, as the histidine molecule becomes protonated and more dicationic with a positive charge on both the α-amino group and imidazole ring, the molecule begins to stabilize the double-stranded DNA structures, promoting hybridization at the positive electrode on the APEX chip. Cations, dications, and polycations are known to help stabilize DNA/DNA hybrids by reducing the repulsion of the negatively charged phosphate backbones on the double-stranded DNA structure. Indeed, upon examining CPK space filling molecular structures of histidine and ds-DNA, the dicationic histidine species, appears to "fit" well to the phosphate oxygen anion spacing along the DNA backbone. Furthermore, examination of CPK space filling structures suggests that di-histidine and other di-, tri-, and polypeptide structures will further significantly stabilize ds-DNA structures. It is believed that in addition to these peptide structures, a large number of peptide derivatives and synthetic structures can be designed to stabilize ds-DNA. It is also possible that the DNA/DNA/Histidine may also form some type of stabilizing adduct from other electrochemical products being produced at the positive electrode (hydrogen peroxide, etc.).

The advantage of the histidine and associated buffers, is particularly important for the APEX microchip type devices. These particular devices are covered with thinner permeation layer (about 1 to 10 microns), as opposed to deep well devices (about 10 to 100 micron permeation layers) and micromachined or macroscopic type devices (sample preparation, complexity reduction, amplification, electronic dot blots, etc.), and are generally used at a lower range of currents (about 10 nA to about 5 uA) and voltages (about 1.2 to about 5 volts). This lower current and voltage reduces transport rate and hybridization efficiency in the higher conductance buffers and electrolytes. Generally, in these cases, DNA transport would be carried out in a low conductance buffer (such as cysteine or alanine) where relatively lower current and voltage still produces rapid DNA transport. Under these conditions, DNA is rapidly accumulated at the test site, but does not hybridize efficiently. After transport in these low conductance buffers, the solution is usually changed to a high salt buffer (>100 mM sodium chloride or sodium phosphate), which then promotes very efficient hybridization of the concentrated target DNA to the DNA probes at a microlocation test site.

While this embodiment utilizes naturally occurring amino acids, such as histidine, this invention is fully applicable to other natural or synthetic compounds that have good buffering capacity, low conductivity (or zwitterionic characteristics) and have properties that allow DNA hybridization to be stabilized by charge stabilization or adduct formation.

Reducing Agents

The addition of a reducing agent to the zwitterionic buffer system also improves DNA transport to the electrodes. The oxidation products at the electrodes, consisting mainly of $O_2(g)$, free radicals, and peroxide species, have been found to contribute to fluorophore, DNA, and permeation layer damage. In addition, oxidation products of buffer components may also deposit on or into the permeation layer and increase the background signal level of the permeation layer above the electrodes. The presence of a reducing agent significantly reduces water oxidation, water oxidation products, and buffer oxidation products at the positive electrode. In particular, the reduction in the generation of $O_2(g)$ bubbles significantly reduces the amount of turbulence in the area immediately surrounding the electrodes, thereby increasing the rate of accumulation of charged particles (e.g., DNA or RNA) to the microlocations. Additionally or alternatively, the presence of the reducing agent allows the application of a higher current to the electrodes, resulting in improved transportation and/or hybridization.

The reducing agent can be, but is not limited to, cysteine, dithitreitol (DTT), β-mercaptoethanol, α-thioglycerol, other thiol-containing reducing agents, and combinations thereof. The addition of a reducing agent to the low conductance zwitterionic buffers provides the additional advantages of providing a low fluorescent signal background (~75%), protective effects for DNA, RNA, etc., and faster transport of charged materials. The concentration of reducing agent in the buffer is about 25-700 mM, alternatively about 25-500 mM, alternatively about 25 mM, alternatively about 50 mM, alternatively about 100 mM, alternatively about 125 mM, alternatively about 150 mM, alternatively about 250 mM, alternatively about 500 mM. The concentration of reducing agent may depend on the salt composition and can be determined by one of ordinary skill in the art.

In one embodiment, the reducing agent has a thiol group. In this case, the reducing agent has no charge at a pH below the pI of the thiol group. Therefore, there is no significant increase (minimal increase) in the conductivity of the buffer solution.

In a preferred embodiment, the reducing agent is α-thioglycerol. Although all of the compounds mentioned above are effective reducing agents, the long carbon chain of α-thioglycerol (for instance, as compared to β-mercaptoethanol) results in lower solution conductivity, lower transference number, and less odor. L-cysteine tends to have a lower rate of DNA binding and a residual background increase. DTT is very expensive compared to α-thioglycerol. β-Mercaptoethanol is toxic and has a distinct odor. α-thioglycerol is nontoxic and has very little to no odor.

When used in combination with at least one zwitterionic species (e.g., histidine) at various concentrations, reducing agents, and α-thioglycerol (seen below) in particular, were found to prevent extensive bubbling on electrode devices.

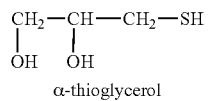

α-thioglycerol

In particular, for APEX devices, the addition of α-thioglycerol was found to prevent bubbling on Pt chip electrodes at currents in excess of 1 μA. FIG. 4 is a graph of oxidation/reduction potential sweeps. The oxidation potential of α-thioglycerol in a solution of 100 mM histidine is less than that necessary for $O_2(g)$ generation from the electrolysis of water in 100 mM histidine. In addition, the potential at which $O_2(g)$ is generated is raised significantly (0.25 Volts) in the presence of α-thioglycerol. Therefore, in the presence of α-thioglycerol, there is sufficient current generated to induce mobility of a charged biomolecule (e.g., DNA or RNA), but $O_2(g)$ generation is substantially reduced in favor of the oxidation of α-thioglycerol.

Additionally, the oxidative products of the reducing agents are less harmful to the electrode devices. The products of water and α-thioglycerol oxidation are depicted in FIG. 5. The generation of hydrogen ions from the oxidation of α-thioglycerol helps consume oxygen and its radicals, reduces the oxidation and formation of polyhistidine adducts, provides hydrogen ions as charge carriers for electrophoresis and reduces the local pH to facilitate hybridization. The oxidation products of α-thioglycerol are water soluble and do not leave a precipitate. For APEX devices, which have a permeation layer coupled to the electrode, such a precipitate is harmful to the permeation layer. FIG. 6 is an electrospray mass spectrum of an electrolyzed histidine buffer solution. The peak at m/z 154.1 corresponds to Histidine (His). The peaks at m/z 309.3 and 463.7 correspond to His adducts, His-His and His-His-His, respectively. FIG. 7 is an electrospray mass spectrum of an electrolyzed histidine buffer solution containing α-thioglycerol. As apparent in a comparison of FIGS. 6 and 7, the His adducts at m/z 309 and 463 are significantly reduced in the presence of α-thioglycerol and peaks corresponding to α-thioglycerol and oxidized adducts of α-thioglycerol are now present. Additionally, a comparison of the mass spectra of the histidine/α-thioglycerol buffer (not electrolyzed, see FIG. 8) to the spectrum of the electrolyzed buffer (see FIG. 7) shows that the buffer components did not change significantly after electrolysis.

Transport of DNA is significantly faster in the presence of reducing agents as a result of the higher currents that can be applied when a buffer containing a reducing agent is used. FIG. 9 is a graph of the accumulation of signal, which corresponds to the amount of DNA transported to a particular microlocation after applying a 400 μA pulse for 1 minute. DNA transport appears to be the faster in α-thioglycerol, as compared to DTT and β-mercaptoethanol. The amount of DNA transported in 250 mM DTT is almost twice as much as compared to 50 mM histidine. The amount of DNA transported in 250 mM β-mercaptoethanol is about four-times as much as compared to 50 mM histidine. And the amount of DNA transported in 250 mM α-thioglycerol is over four-times as much as compared to 50 mM histidine.

In addition, α-thioglycerol does not significantly increase the conductivity of histidine buffers. At working concentrations, α-thioglycerol contributes <35% to the conductivity of Histidine buffer solutions (see Table 3).

TABLE 3

| Buffer | Conductivity (μS/cm) | Std. Dev. |
|---|---|---|
| Water | 0 | 0 |
| 100 mM Histidine | 114 | 9 |
| 50 mM Histidine | 56 | 3 |
| 100 mM Histidine/250 mM α-thioglycerol | 158 | 1 |
| 50 mM Histidine/125 mM α-thioglycerol | 83 | 2 |
| Conductivity Contribution at 250 mM α-thioglycerol | 44 (28%) | |
| Conductivity Contribution at 125 mM α-thioglycerol | 27 (33%) | |

The addition of a reducing agent results in a lower background signal as compared with a buffer without the reducing agent. Table 4 reports the signals where target oligos P1, P2, P3, FA, and FB were sequentially biased to specific sites on the chip and allowed to hybridize to capture oligos FA, RB, RA, and IC (internal control). As seen for Target FA, hybridization only occurred with capture oligo FA. Additionally, the background signal for all of the other target oligos are lower in the buffer with α-thioglycerol as compared to the buffer without α-thioglycerol.

TABLE 4

| Target | Buffer w/α-thioglycerol | | | | Buffer w/out α-thioglycerol | | | |
|---|---|---|---|---|---|---|---|---|
| | FA | RB | RA | IC | FA | RB | RA | IC |
| 2 μl P1 | 17 | 1 | 21 | 1 | 5 | 1 | 6 | 1 |
| 4 μl P1 | 38 | 2 | 37 | 2 | 7 | 1 | 10 | 1 |
| 8 μl P1 | 47 | 2 | 47 | 2 | 9 | 1 | 9 | 1 |
| 2 μl P2 | 25 | 10 | 23 | 10 | 8 | 3 | 6 | 2 |
| 4 μl P2 | 26 | 14 | 26 | 14 | 7 | 3 | 4 | 2 |
| 8 μl P2 | 28 | 18 | 25 | 17 | 6 | 3 | 4 | 2 |
| 2 μl P3 | 27 | 47 | 27 | 40 | 8 | 12 | 7 | 8 |
| 4 μl P3 | 29 | 59 | 31 | 57 | 15 | 14 | 10 | 9 |
| 8 μl P3 | 40 | 83 | 40 | 78 | 16 | 16 | 11 | 13 |
| 2 μl FA | 534 | 1 | 25 | 1 | 486 | 1 | 21 | 1 |
| 4 μl FA | 577 | 1 | 31 | 1 | 560 | 1 | 11 | 1 |
| 8 μl FA | 569 | 1 | 39 | 1 | 658 | 1 | 12 | 1 |
| 2 μl FB | 77 | 10 | 20 | 7 | 81 | 4 | 12 | 3 |
| 4 μl FB | 30 | 13 | 28 | 13 | 18 | 4 | 14 | 4 |
| 8 μl FB | 32 | 17 | 34 | 17 | 19 | 4 | 23 | 6 |
| 2 μl RA | 15 | 6 | 502 | 5 | 5 | 2 | 534 | 2 |
| 4 μl RA | 19 | 6 | 642 | 6 | 12 | 4 | 684 | 2 |
| 8 μl RA | 25 | 8 | 747 | 8 | 7 | 3 | 632 | 3 |

Heat Denaturation

Experiments also suggest that the reducing agent, in this case α-thioglycerol, may act as a chaotropic agent. As seen in Table 5, there is no significant change in signal intensity when target samples P1, P3, INF B, INF A, and RSV A were addressed in the zwitterionic buffer containing α-thioglycerol with and without the heat denaturation step. Therefore, it appears that the target samples that were not subjected to heat denaturation were denatured by the buffer containing the reducing agent.

TABLE 5

| Target | Heat Denaturation | Cartridge 1 | Cartridge 2 |
|---|---|---|---|
| P1 | yes | 251 | 277 |
| P1 | no | 183 | 211 |
| P3 | yes | 2453 | 2014 |
| P3 | no | 1915 | 1974 |
| INF B | yes | 563 | 405 |
| INF B | no | 483 | 272 |
| INF A | yes | 852 | 750 |
| INF A | no | 546 | 464 |
| RSV A | yes | 759 | 994 |
| RSV A | no | 931 | 911 |

Although the foregoing invention has been described in some detail by way of illustration and example for purposes of clarity and understanding, it will be readily apparent to those of ordinary skill in the art in light of the teachings of this invention that certain changes and modifications may be made thereto without departing from the spirit or scope of the appended claims.

What is claimed is:

1. A method for the transport of a nucleic acid to an electrode site comprising the steps of:
   providing a nucleic acid and a low conductivity, zwitterionic buffer with a reducing agent to an active electronic system comprising an electrode;
   applying current and voltage to the electrode to effect electrophoretic transportation of the nucleic acid towards the electrode; and
   hybridizing the nucleic acid with a probe located at the electrode, whereby the local pH above the electrode is below the pH of the buffer at its isoelectric point.

2. The method of claim 1, wherein the reducing agent is α-thioglycerol.

3. The method of claim 1, wherein the reducing agent is dithiotreitol.

4. The method of claim 1, wherein the reducing agent is β-mercaptoethanol.

5. The method of claim 1, wherein a concentration of the reducing agent is about 25-500 mM.

6. The method of claim 1, wherein a concentration of the reducing agent is about 25 mM.

7. The method of claim 1, wherein a concentration of the reducing agent is about 125 mM.

8. The method of claim 1, wherein a concentration of the reducing agent is about 150 mM.

9. The method of claim 1, wherein a concentration of the reducing agent is about 250 mM.

10. The method of claim 1, wherein a concentration of the reducing agent is about 500 mM.

11. The method of claim 1, wherein the low conductivity, zwitterionic buffer is histidine.

12. The method of claim 11, wherein the low conductivity, zwitterionic buffer further comprises an additional zwitterion.

13. The method of claim 1, wherein the low conductivity, zwitterionic buffer contains L-histidine.

14. The method of claim 1, wherein the low conductivity, zwitterionic buffer contains D-histidine.

15. The method of claim 1, wherein the low conductivity, zwitterionic buffer contains cysteine.

16. The method of claim 1, wherein the low conductivity, zwitterionic buffer contains alanine.

17. The method of claim 1, wherein the low conductivity, zwitterionic buffer contains lysine.

18. The method of claim 1, wherein the low conductivity, zwitterionic buffer contains glutamic acid.

19. The method of claim 1, wherein the low conductivity, zwitterionic buffer contains γ-aminobutyric acid.

* * * * *